United States Patent [19]

Reddy

[11] Patent Number: 5,027,831
[45] Date of Patent: Jul. 2, 1991

[54] PROPHYLACTIC WITH GLANS PENIS STIMULATION

[76] Inventor: A. V. K. Reddy, 9 Webster Ct., Plainsboro, N.J. 08536

[21] Appl. No.: 526,843

[22] Filed: May 22, 1990

[51] Int. Cl.$^5$ ............................................... A61F 6/04
[52] U.S. Cl. .................................... 128/844; 128/918
[58] Field of Search ................. 128/842, 844, 79, 918; 604/330, 347–353

[56] References Cited

U.S. PATENT DOCUMENTS

| | | | |
|---|---|---|---|
| 2,326,159 | 8/1943 | Mendel | 604/349 |
| 2,410,460 | 11/1946 | Robinson | 128/844 |
| 2,577,345 | 12/1951 | McEwen | 604/349 |
| 2,586,674 | 2/1952 | Lönne | 604/349 |
| 2,816,542 | 12/1957 | Freeman | 128/844 |
| 3,463,141 | 8/1969 | Mozolf | 128/842 |
| 3,809,090 | 5/1974 | Poulacs | 604/349 |
| 4,820,290 | 4/1989 | Yahr | 604/349 |
| 4,919,149 | 4/1990 | Stang | 604/349 |

FOREIGN PATENT DOCUMENTS

| | | | |
|---|---|---|---|
| 2620729 | 11/1977 | Fed. Rep. of Germany | 128/844 |
| 0859835 | 12/1940 | France | 604/349 |
| 0326719 | 3/1930 | United Kingdom | 604/349 |

*Primary Examiner*—Robert A. Hafer
*Assistant Examiner*—Michael Brown
*Attorney, Agent, or Firm*—Reising, Ethington, Barnard, Perry & Milton

[57] ABSTRACT

A male prophylactic has a tubular pouch with a closed end and an open end and an integrally formed pouch on the pouch at the closed end defining a spaced pouch on pouch for a sensitive undersurface portion of the glans penis. The pouch on the pouch is configured to be movable back and forth on the surface of the underside of the glans penis from approximately ½ cm below the urethra orifice to a point approximately 2 cm from the orifice. The pouch on the pouch moves to stroke and stimulate the glans penis during coitus.

2 Claims, 1 Drawing Sheet

PROPHYLACTIC WITH GLANS PENIS STIMULATION

FIELD OF THE INVENTION

This invention relates to prophylactic or birth control devices and in particular to such devices designed for the mate partner in coitus.

BACKGROUND OF THE PRIOR ART

A wide variety of male condoms or prophylactic devices are known for use in disease prevention and to safeguard against pregnancy. In the past such devices have been tight fitting to prevent accidental dislodgment during coitus. Furthermore, in order to be rupture proof the wall thickness of membrane material forming the pouch of such male condoms has resulted in loss of sensation by the male user during coitus.

Other loose fitting condoms have been proposed for female use including U.S. Pat. Nos. 4,004,591 and 3,536,066. Both of these patents disclose pouches of a diameter much larger than that of the glans penis and they do not include pouch on pouch means capable of producing stimulation of the surface of a glans penis during coitus.

U.S. Pat. No. 2,816,542 discloses a condom with a thickened wall portion at the condom tip for stimulation.

U.S. Pat. No. Des. 254,808 issued Apr. 22, 1980 discloses an ornamental design in which the pouch of a male condom has outwardly directed bulges. However, the bulges are not arranged so as to stimulate the surface of a glans penis during coitus.

None of the aforesaid patents include a condom with a pouch on pouch arranged to produce a rolling action on the most sensitive region of the glans penis.

STATEMENT OF INVENTION AND ADVANTAGES

The AIDS epidemic has caused more people to consider the use of condoms for protection against transmission of AIDS and other social diseases. Prior condoms, however, have resulted in less sensation and, as a consequence, their use is often omitted. The purpose of this invention is to provide an improved condom which will be more acceptable to male users and, therefore, more widely used because of increased user sensation.

It is an object of the present invention to provide a male condom which will be more acceptable to the male user by providing enhanced sensation during coitus.

In order to solve the problem of insensitivity the condom of the present invention is configured to take advantage of the recognized greater sensitivity of the glans penis during coitus.

To this end, the condom includes a pouch on pouch in the thin membrane material of the condom that will move back and forth on the underside region of the glans penis during coitus to provide enhanced stimulation and sensitivity to the male user of the condom.

A feature of the present invention is to solve the insensitivity problem in male condoms by providing an elongated tubular pouch of thin membrane material and having a generally constant diameter from the open end to the closed end and by the further feature of pouch on pouch means integrally formed on the circumference of the closed end to form a pocket overlying in spaced relationship to the ventral or underside region of the glans penis and movable back and forth thereon during coitus for providing stimulation thereto.

A further feature is to provide such pouch on pouch means formed through only a part of the circumference to produce movement only on part of the surface of the glans penis, e.g., the underside of the glans penis.

A still further feature is to provide such pouch on pouch means formed on the circumference of the closed end completely around the circumference to produce movement on all of the surface of the glans penis.

Yet another feature of the invention is to provide such a condom in which the pouch is formed of fine rubber or plastic material and the pouch on pouch means is formed as a side bulge in the circumference of the closed end.

A further feature of the invention is to provide such a condom wherein the pouch is characterized by the side bulge being formed as a hollow conoidally shaped bulge.

Yet another feature of the present invention is to provide such a condom wherein the pouch is characterized by the side bulge being formed as a hollow ring around the closed end of the pouch.

Other advantages of the present invention will be readily appreciated as the same becomes better understood by reference to the following detailed description when consider in connection with the accompanying drawings wherein:

Detailed Description of Preferred Embodiments

Figure 1:
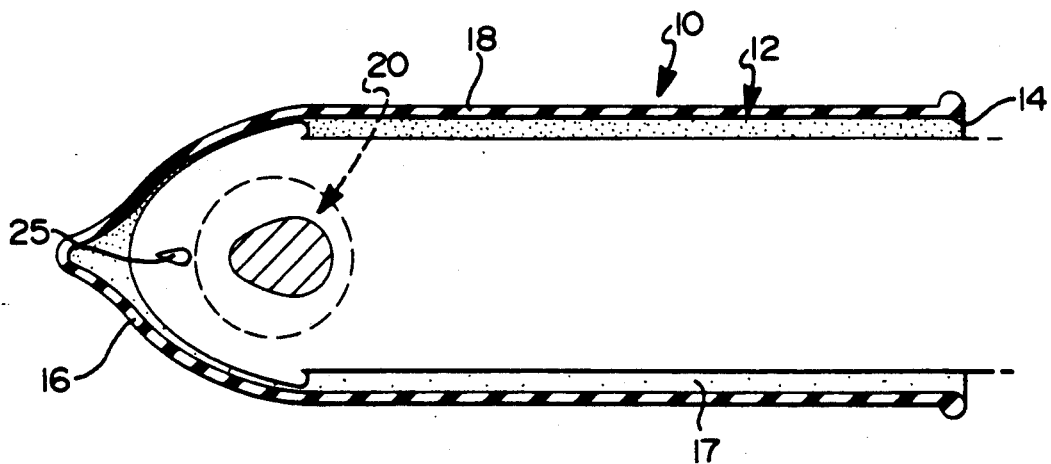
FIG. 1 is a sectional view of a male condom including one embodiment of the present invention.
Figure 2:
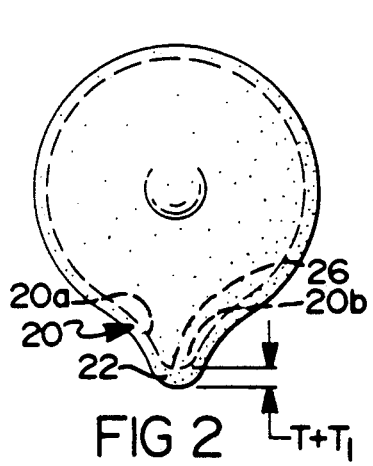
FIG. 2 is an end elevational view of the male condom of FIG. 1.

FIGS. 1 and 2 illustrate a male condom 10 having a tubular pouch 12 with an open end 14 and a closed end 16. The pouch 12 has a diameter which will closely fit on the outer surface of a penis whose glans penis will be located within the pouch in spaced relationship to the closed end 16. The pouch 12 is of generally constant diameter between the open end 14 and the closed end 16 to define a longitudinally directed chamber 17. The pouch 12 has a thin membrane wall 18 that will enhance sensation to the male user during use but which will retain enough strength to prevent rupture of the wall 18 during use for protection against AIDS or other social diseases.

Figure 3:
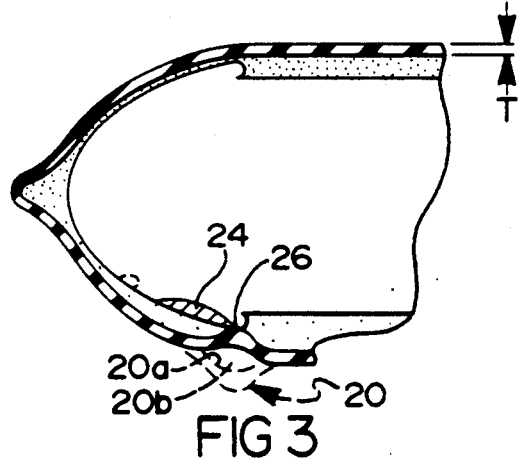
FIG. 3 is a fragmentary sectional view of the condom of FIGS. 1 and 2 showing a pouch on pouch stroked inwardly.

In accordance with certain principles of the present invention the pouch 12 includes a glans penis pouch on pouch 20 which in the embodiment of FIGS. 1 and 2 is in the form of a considally configured wall bulge 22 extending outwardly of only one side of the pouch 12 adjacent the closed end 16. As best shown in FIG. 3, the pouch 20 has an entrance opening 20a through which the chamber 17 is communicated with an interior space 20b of the pouch 20. Thus the second pouch 20 is formed on one side of the pouch 12 at a point overlying and in spaced relationship to the most sensitive surface 24 of the glans penis starting approximately ½ cm from the outlet 25 from the urethra and ending at a point 2 cm from the outlet 25 as shown in shaded outline in FIG. 1.

Specifically, the wall bulge 22 has a conoidal surface 26 which will be pushed inwardly during coitus to move back and forth on the glans penis surface 24 as shown in the enlarged fragmentary sectional view of FIG. 3. The back and forth movement will stimulate the glans penis so as to provide enhanced sensation to the male user of the condom 10. While the pouch on pouch 20 can have the same thickness T as the pouch wall 18, as shown in FIG. 1, the thickness of pouch on pouch 20 is $T+T_1$.

Figure 4:
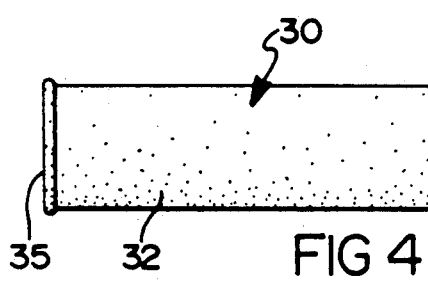
FIG. 4 is a side elevational view of a male condom including another embodiment of the present invention.
Figure 5:
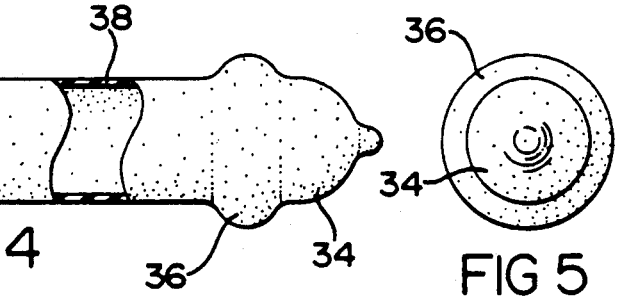
FIG. 5 is an end elevational view of the male condom of FIG. 3.
Figure 6:
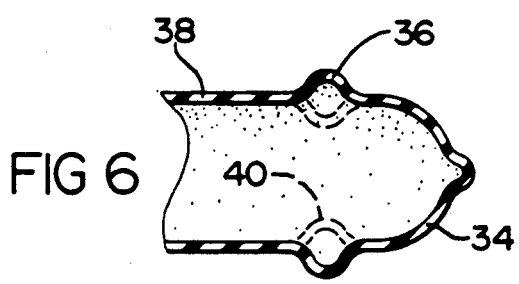
FIG. 6 is a fragmentary sectional view of FIGS. 5 and 6 showing the pouch on pouch stroked inwardly.

In the embodiment of FIGS. 4–6 a male condom 30 is shown with a thin membrane tubular pouch 32 having a closed end 34 and an open end 36. The diameter of the pouch 32 closely fits to the outer surface of a male penis such that the glans penis is located in spaced relationship to the closed end 34.

In this embodiment the glans penis pouch on pouch is in the form of a hollow ring 36 formed integrally of the wall 38 of the pouch 32 around the circumference of the glans penis in spaced relationship therewith. During coitus a circular surface 40 of the hollow ring 36 moves back and forth on the surface 24 of the glans penis.

In the various embodiments of prophylactic devices of this invention, the sizes of the pouches and wall thicknesses of the materials may vary. The tubular pouches may have a length in the range of 160 mm. Although the diameter of the pouch is generally uniform it could vary if desired. In the main body portion, the diameter is approximately 105 mm. The diameter at the pouch on the pouch is in the range of 115 mm±10 mm. However, the glans penis pouch on pouch is dimensioned to provide a space prior to insertion and a reversal of the pouch on pouch inwardly during coitus to provide a back and forth movement in engagement with the surface of the glans penis.

The thickness of the wall material of the pouch may also vary. Preferably the wall thickness is in the range of 0.1 mm–0.03 mm to+1 mm +0.3 mm. The pouch and entrance flange are preferably made of elastic, impermeable material such as natural rubber, synthetic rubber such as silicone rubber. Other useful materials include plastic such as polyurethane, polyvinyl chloride or polyethylene.

While the invention has been described in an illustrative manner it should be understood that the invention may be practiced other than as specifically described herein and yet remain within the scope of the appended claims.

What is claimed is:

1. A male condom comprising an elongated tubular portion formed by a thin elastic membrane forming a first pouch having an open end and a closed end and a tubular wall formed therebetween having a substantially constant diameter;

said tubular portion defining a longitudinally directed chamber for receiving a male penis and said tubular wall covering the penis along its length;

a second pouch formed of thin membrane material extending outwardly of only one side of said first pouch;

said second pouch having an interior space and formed integrally of said first pouch and including an entrance which communicates said interior space directly with said longitudinally directed chamber at a point located in overlying relationship to the glans penis of the male penis located within said longitudinally directed chamber;

said thin membrane material of said second pouch having an inner surface exposed through and movable through said entrance for contact with the glans penis for movement of the thin membrane material of said second pound back and forth thereon during coitus for mechanically stroking the glans penis so as to provide stimulation thereto.

2. A male condom comprising a elongated tubular portion formed by a thin elastic membrane forming a first pouch having an open end and a closed end and a tubular wall formed therebetween having a substantially constant diameter;

said tubular portion defining a longitudinally directed chamber for receiving a male penis and said tubular wall covering the penis along its length;

a second pound formed of thin membrane material extending outwardly of only one side of said first pouch and shaped as a hollow conoidally configured bulge on one said of said first pouch adjacent said closed end thereof;

said second pouch having an interior space and formed integrally of said first pouch and including an entrance which communicates said interior space directly with said longitudinally directed chamber at a point located in overlying relationship to the glans penis of the male penis located within said longitudinally directed chamber;

said thin membrane material of said second pouch being exposed through said entrance for contact with the glans penis for rolling movement of the thin membrane material of said second pouch back and forth thereacross during coitus for mechanically stroking the glans penis so as to provide stimulation thereto.

* * * * *